United States Patent
Weber et al.

(10) Patent No.: US 10,898,500 B2
(45) Date of Patent: Jan. 26, 2021

(54) COMBINATION OF REGORAFENIB AND ACETYLSALICYLIC ACID FOR TREATING CANCER

(71) Applicants: BAYER PHARMA AKTIENGESELLSCHAFT, Berlin (DE); BAYER AG, Leverkusen (DE)

(72) Inventors: Olaf Weber, Wülfrath (DE); Karl Ziegelbauer, Haan (DE)

(73) Assignees: BAYER PHARMA AKTIENGESELLSCHAFT, Berlin (DE); BAYER AG, Leverkusen (DE)

(*) Notice: Subject to any disclaimer, the term of this patent is extended or adjusted under 35 U.S.C. 154(b) by 0 days.

(21) Appl. No.: 14/431,119

(22) PCT Filed: Sep. 23, 2013

(86) PCT No.: PCT/EP2013/069735
§ 371 (c)(1),
(2) Date: Mar. 25, 2015

(87) PCT Pub. No.: WO2014/048881
PCT Pub. Date: Apr. 3, 2014

(65) Prior Publication Data
US 2015/0202214 A1 Jul. 23, 2015

(30) Foreign Application Priority Data
Sep. 25, 2012 (EP) ...................................... 12185852

(51) Int. Cl.
*A61K 31/616* (2006.01)
*A61K 31/44* (2006.01)

(52) U.S. Cl.
CPC ............ *A61K 31/616* (2013.01); *A61K 31/44* (2013.01)

(58) Field of Classification Search
CPC ................................ A61K 31/616; A61K 31/44
See application file for complete search history.

(56) References Cited

U.S. PATENT DOCUMENTS

| | | | |
|---|---|---|---|
| 6,620,834 B1 * | 9/2003 | Tanida .................... | A61K 31/22 514/252.06 |
| 8,637,553 B2 | 1/2014 | Boyer et al. | |
| 8,748,622 B2 | 6/2014 | Stiehl et al. | |
| 2004/0121004 A1 | 6/2004 | Taneja | |
| 2005/0038080 A1 | 2/2005 | Boyer et al. | |
| 2009/0074863 A1 | 3/2009 | Taneja | |
| 2009/0192127 A1 | 7/2009 | Scheuring et al. | |
| 2010/0173953 A1 | 7/2010 | Gruenberg et al. | |
| 2013/0116442 A1 | 5/2013 | Stiehl et al. | |
| 2013/0131122 A1 | 5/2013 | Boyer et al. | |
| 2014/0221661 A1 | 8/2014 | Stiehl et al. | |
| 2014/0315958 A1 | 10/2014 | Gruenberg et al. | |

FOREIGN PATENT DOCUMENTS

| | | | | |
|---|---|---|---|---|
| WO | 2005009961 A2 | 2/2005 | | |
| WO | WO 2005009961 A2 * | 2/2005 | ............ | C07D 213/81 |
| WO | WO-2005009961 A2 * | 2/2005 | ............. | C07D 13/81 |
| WO | 2007054303 A2 | 5/2007 | | |
| WO | WO 2007054303 A2 * | 5/2007 | ......... | A61K 31/4412 |
| WO | WO-2007054303 A2 * | 5/2007 | ......... | A61K 31/4412 |
| WO | 2008043446 A1 | 4/2008 | | |
| WO | WO-2011098839 A2 * | 8/2011 | ............. | A61K 31/60 |
| WO | 2011128261 A1 | 10/2011 | | |

OTHER PUBLICATIONS

Wilhelm et al.,(International Journal of Cancer, vol. 129 pp. 245-255, published 2011).*
Antonetti et al., NEJM vol. 366 pp. 1227-1239. Published 2012.*
Starke et al (Carcinogenesis vol. 28, pp. 968-976, published 2007).*
Stedman Medical Dictionary 27st edition (Published 2001).*
Sandler, R.S., et al., New England Journal of Medicine vol. 348 883-890. Published 2003.*
Reagan-Shaw et al., FASEB J vol. 22 659-661. Published 2007.*
Wilhelm et al (International Journal of Cancer, vol. 129, pp. 245-255, published online Dec. 2010, referred to as Wilhelm_A).*
Asprin Product Page (Bayer).*
Sandler et al (New England Journal of Medicine vol. 348 pp. 883-890 published 2003) (Year: 2003).*
Wilhelm et al (Int. J. Cancer vol., 129 ages 245-255 published 2011) (Year: 2011).*
MSDS of o-acetylsalicylic acid. CDH Chemicals (Year: 2018).*
Walpole et al., BMC Public Health vol. 12 pp. 439-445. Published online Jun. 18, 2012 (Year: 2012).*
Wilhelm., International Journal of Cancer, vol. 129, pp. 245-255, published online Dec. 2010 (Year: 2010).*
Pathi et al., PLOSone vol. 7 pp. e48208(1)-e48208(14) published online Oct. 26, 2012 (Year: 2012).*
Ivy et al., Clinical Cancer Research vol. 16 pp. 1726-1736. Published 2010. (Year: 2010).*
Walpole et al., BMC Public Health vol. 12 pp. 439-445 published Jun. 2012 (Year: 2012).*
Wilhelm et al., International Journal of Cancer, vol. 129, pp. 245-255, published online Dec. 2010 (Year: 2010).*
Rothwell P.M. et al, "Short-term effects of daily aspirin on cancer incidence, mortality, and non-vascular death: analysis of the time course of risks and benefits in 51 randomised controlled trials" Lancet, [2012], vol. 379, pp. 1602-1612.
Rothwell P.M. et al, "Effect of daily aspirin on risk of cancer metastasis: a study of incident cancers during randomised controlled trials" Lancet, [2012], vol. 379, pp. 1591-1601.
International Search Report from PCT/EP2013/069735 dated Nov. 5, 2013.
IPRP and Written Opinion from PCT/EP2013/069735 dated Mar. 31, 2015.

(Continued)

*Primary Examiner* — Timothy P Thomas
*Assistant Examiner* — George W Kosturko
(74) *Attorney, Agent, or Firm* — Millen White Zelano and Branigan, PC

(57) ABSTRACT

The present invention relates to pharmaceutical compositions and combinations comprising regorafenib and acetylsalicylic acid, or a hydrate, solvate, metabolite or pharmaceutically acceptable salt thereof or a polymorph thereof for treating, preventing or managing diseases and conditions including hyperproliverative disorders such as cancer in humans and other mammals.

4 Claims, No Drawings

(56) References Cited

OTHER PUBLICATIONS

John Burn et al. "Long-term effect of aspirin on cancer risk in carriers of hereditary colorectal cancer: an analysis from the CAPP2 randomised controlled trial" Lancet, Elsevier, (2011), vol. 378, No. 9809, pp. 2081-2087.

Axel Grothey et al. "Regorafenib monotherapy for previously treated metastatic colorectal cancer (CORRECT): an international, multicentre, randomised, placebo-controlled, phase 3 trial" Lancet, (2013), vol. 381, No. 9863, pp. 303-312.

Rohwer et al.; Effects of chronic low-dose aspirin treatment on tumor prevention in three mouse models of intestinal tumorigenesis; Cancer Med. 2020;00:pp. 1-16; Jan. 13, 2020.

* cited by examiner

COMBINATION OF REGORAFENIB AND ACETYLSALICYLIC ACID FOR TREATING CANCER

The present invention relates to pharmaceutical compositions and combinations comprising regorafenib and acetylsalicylic acid, or a hydrate, solvate, metabolite or pharmaceutically acceptable salt thereof or a polymorph thereof for treating, preventing or managing diseases and conditions including hyperproliverative disorders such as cancer in humans and other mammals.

Regorafenib which is 4{4-[3-(4-chloro-3-trifluoromethylphenyl)-ureido]-3-fluorophenoxy}-pyridine-2-carboxylic acid methylamide, a compound of formula (I)

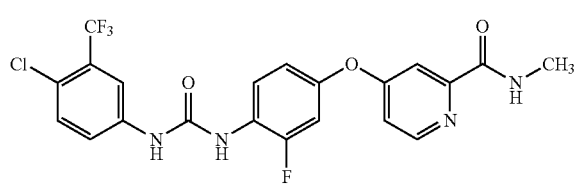

(I)

is a potent anti-cancer and anti-angiogenic agent that possesses various activities including inhibitory activity on the VEGFR, PDGFR, raf, p38, and/or flt-3 kinase signalling molecules and it can be used in treating various diseases and conditions like hyper-proliferative disorders such as cancers, tumors, lymphomas, sarcomas and leukemias as described in WO 2005/009961. It is currently developed for the treatment of colorectal cancer and gastrointestinal stromal tumors. Furthermore salts of the compound of formula (I) such as its hydrochloride, mesylate and phenylsulfonate are mentioned in WO 2005/009961. The monohydrate of the compound of formula (I) is mentioned in WO 2008/043446. An improved process for the manufacturing of regorafenib in high purity is described in WO 2011/128261.

Acetylsalicylic acid is a well-known drug which cannot only be used for treating pain or reducing the risk to develop a cardiovascular event or disease but there are also hints for reducing the risk of developing cancer diseases (Rothwell P M et al (2012) Short-term effects of daily acetylsalicylic acid on cancer incidence, mortality and non-vascular death: analysis of the time course of risks and benefits in 51 randomized controlled trials. Lancet. 379: 1602-1612).

Furthermore acetylsalicylic acid can reduce metastasis of tumors effecting a reduction of mortality in particular in patients with colorectal cancer (Rothwell P M et al (2012) Effect of daily acetylsalicylic acid on risk of cancer metastasis: a study of incident cancers during randomised controlled trials. Lancet. 379: 1591-1601).

Object of the present invention is the improvement of the cancer therapy by the administration of regorafenib and acetylsalicylic acid in combination.

Surprisingly the combination of regorafenib and acetylsalicylic acid shows a significant efficacy improvement over the sum of the monotherapies. Furthermore the profile of the side effects (e.g. hand-foot syndrome, elevated blood pressure, fatigue, diarrhea and mucosal inflammation) can be improved.

The present invention pertains to a combination comprising regorafenib which is the compound of the formula (I)

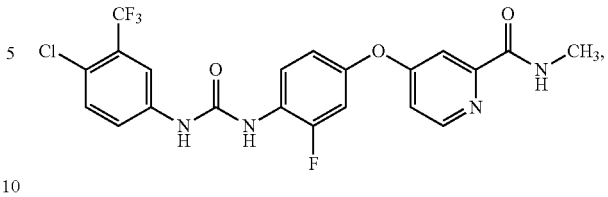

(I)

and acetylsalicylic acid, or a hydrate, solvate, metabolite or pharmaceutically acceptable salt of thereof, or a polymorph thereof.

The term "the compound of formula (I)" or "regorafenib" refer to 4-{4-[({[4-chloro-3-(trifluoromethyl)phenyl]amino}carbonyl)amino]-3-fluorophenoxy}-N-methylpyridine-2-carboxamide as depicted in formula (I).

Solvates for the purposes of the invention are those forms of the compounds or their salts where solvent molecules form a stoichiometric complex in the solid state and include, but are not limited to for example water, ethanol and methanol.

Hydrates are a specific form of solvates, where the solvent molecule is water. Hydrates of the compounds of the invention or their salts are stoichiometric compositions of the compounds or salts with water, such as, for example, hemi-, mono- or dihydrates. Preference is given to the monohydrate of regorafenib.

Salts for the purposes of the present invention are preferably pharmaceutically acceptable salts of the compounds according to the invention. Suitable pharmaceutically acceptable salts are well known to those skilled in the art and include salts of inorganic and organic acids, such as hydrochloric acid, hydrobromic acid, sulfuric acid, phosphoric acid, methanesulphonic acid, trifluoromethanesulfonic acid, benzenesulfonic acid, p-toluenesulfonic acid (tosylate salt), 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU). Preference is given to the hydrochloride, mesylate or phenylsulfonate salt of regorafenib.

Metabolites of regorafenib for the purpose of the present invention include 4-[4-({[4-chloro-3-(trifluoromethyl)phenyl]carbamoyl}amino)-3-fluorophenoxy]-N-methylpyridine-2-carboxamide 1-oxide, 4-[4-({[4-chloro-3-(trifluoromethyl)phenyl]carbamoyl}amino)-3-fluorophenoxy]-N-(hydroxymethyl)pyridine-2-carboxamide, 4-[4-({[4-chloro-3-(trifluoromethyl)phenyl]carbamoyl}amino)-3-fluorophenoxy]pyridine-2-carboxamide and 4-[4-({[4-chloro-3-(trifluoromethyl)phenyl]carbamoyl}amino)-3-fluorophenoxy]pyridine-2-carboxamide 1-oxide.

Preferred are regorafenib and the monohydrate of regorafenib as a compound of the present invention.

The compounds of the invention may be prepared by use of known chemical reactions and procedures.

Method for Treatment:

The present invention also relates to a method for using the combination and compositions thereof, to treat mammalian hyper-proliferative disorders. This method comprises administering to a mammal in need thereof, including a human, an amount of the combination, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small intestine, and salivary gland cancers.

Preference is given to colorectal cancer.

Preference is also given to gastrointestinal stromal tumors (GIST).

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Preference is given to hepatic cell cancer.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The present invention further provides the use of the compound of the invention for the preparation of a pharmaceutical compositions for the treatment of the aforesaid disorders.

Administration

Combinations of the present invention can be administered in any form by any effective route, including, e.g., oral, parenteral, enteral, intravenous, intraperitoneal, topical, transdermal (e.g., using any standard patch), ophthalmic, nasally, local, non-oral, such as aerosol, inhalation, subcutaneous, intramuscular, buccal, sublingual, rectal, vaginal, intra-arterial, and intrathecal, etc. They can be administered alone, or in combination with any ingredient(s), active or inactive.

Preference is given to an oral administration.

Alternatively acetylsalicylic acid can be administered intravenously.

Combinations of the present invention can be converted in a known manner into the usual formulations, which may be liquid or solid formulations e.g. without limitation normal and enteric coated tablets, capsules, pills, powders, granules, elixirs, tinctures, solution, suspensions, syrups, solid and liquid aerosols and emulsions.

Examples of solid formulations for oral administration are described in U.S. provisional application No. 60/605,752.

Generally, the use of the combinations of the present invention mentioned before will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects, "Combination" means for the purposes of the invention not only a dosage form which contains all the components (so-called fixed combinations), and combination packs containing the components separate from one another, but also components which are administered simultaneously or sequentially, as long as they are employed for the prophylaxis or treatment of the same disease.

The amount of the administered active ingredient can vary widely according to such considerations as the particular compound and dosage unit employed, the mode and time of administration, the period of treatment, the age, sex, and general condition of the patient treated, the nature and extent of the condition treated, the rate of drug metabolism and excretion, the potential drug combinations and drug-drug interactions, and the like.

An aspect of the invention of particular interest is a combination comprising regorafenib in an amount of 4 to 400 mg, preferably from 10 to 200 mg, more preferably from 10 to 100 mg.

A further aspect of the invention of particular interest is a combination comprising acetylsalicylic acid in an amount of 50 to 100 mg, preferably from 60 to 500 mg, more preferably from 70 to 350 mg. Typical doses of acetylsalicylic acid are 78 mg, 81 mg, 100 mg, 325 mg, 500 mg and 1000 mg.

The daily dose of regorafenib is from 10 to 1000 mg, preferably 40 to 500 mg, more preferably 80 to 320 mg, e.g. 160 mg.

The daily dose of acetylsalicylic acid is from 50 to 1000 mg, preferably from 60 to 500 mg, more preferably from 70 to 350 mg. Typical daily doses of acetylsalicylic acid are 78 mg, 81 mg, 100 mg, 325 mg, 500 mg and 1000 mg.

The pharmaceutical composition according to the invention is administered one or more, preferably up to three, more preferably up to two times per day. Preference is given to an administration via the oral route. With each administration the number of tablets or capsules taken in at the same time should not exceed two.

Nevertheless, it may in some cases be advantageous to deviate from the amounts specified, depending on body weight, individual behaviour toward the active ingredient, type of preparation and time or interval over which the administration is affected. For instance, less than the aforementioned minimum amounts may be sufficient in some cases, while the upper limit specified has to be exceeded in other cases. In the case of administration of relatively large amounts, it may be advisable to divide these into several individual doses over the day.

Examples of an administration scheme are as follows: In the first cycle daily doses of 160 mg regorafenib and 81 mg acetylsalicylic acid are administered for 3 weeks. In week four only 81 mg acetylsalicylic acid are administered. Then the cycle can be repeated. Alternatively the daily dose of acetylsalicylic acid can be equal or less than 325 mg (e.g. 100 mg) or it can be more than 325 mg (e.g. 500 mg).

The combination can comprise effective amounts of the compound of Formula I and acetylsalicylic acid, which achieves a greater therapeutic efficacy than when either compound is used alone.

The relative ratios of each compound in the combination can also be selected based on their respective mechanisms of action and the disease biology. The relative ratios of each compound can vary widely.

The release of one or more agents of the combination can also be controlled, where appropriate, to provide the desired therapeutic activity when in a single dosage form, combination pack, kit or when in separate independent dosage forms.

The present invention includes pharmaceutical compositions which are comprised of a pharmaceutically acceptable carrier and a pharmaceutically effective amount of the compounds of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated.

For oral administration, the compounds can be formulated into solid or liquid preparations such as solid dispersion, capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain anon-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent, Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A compositions of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material is, for example, cocoa butter and polyethylene glycol.

Controlled release formulations for parenteral administration include liposomal, polymeric microsphere and polymeric gel formulations which are known in the art.

The pharmaceutical compositions of this invention may also be in the form of a solid dispersion. The solid dispersion may be a solid solution, glass solution, glass suspension, amorphous precipitation in a crystalline carrier, eutectic or monotecic, compound or complex formation and combinations thereof.

An aspect of the invention of particular interest is a pharmaceutical composition comprising a solid dispersion, wherein the matrix comprises a pharmaceutically acceptable polymer, such as polyvinylpyrrolidone, vinylpyrrolidone/vinylacetate copolymer, polyalkylene glycol (i.e. polyethylene glycol), hydroxyalkyl cellulose (i.e. hydroxypropyl cellulose), hydroxyalkyl methyl cellulose (i.e. hydroxypropyl methyl cellulose), carboxymethyl cellulose, sodium carboxymethyl cellulose, ethyl cellulose, polymethacrylates, polyvinyl alcohol, polyvinyl acetate, vinyl alcohol/vinyl acetate copolymer, polyglycolized glycerides, xanthan gum, carrageenan, chitosan, chitin, polydextrin, dextrin, starch and proteins.

Another aspect of the invention is a pharmaceutical composition comprising a solid dispersion, wherein the matrix comprises a sugar and/or sugar alcohol and/or cyclodextrin, for example sucrose, lactose, fructose, maltose, raffinose, sorbitol, lactitol, mannitol, maltitol, erythritol, inositol, trehalose, isomalt, inulin, maltodextrin, β-cyclodextrin, hydroxypropyl-β-cyclodextrin or sulfobutyl ether cyclodextrin.

Additional suitable carriers that are useful in the formation of the matrix of the solid dispersion include, but are not limited to alcohols, organic acids, organic bases, amino acids, phospholipids, waxes, salts, fatty acid esters, polyoxyethylene sorbitan fatty acid esters, and urea.

The solid dispersion of regorafenib in the matrix may contain certain additional pharmaceutical acceptable ingredients, such as surfactants, fillers, disintegrants, recrystallization inhibitors, plasticizers, defoamers, antioxidants, detackifier, pH-modifiers, glidants and lubricants.

The solid dispersion of the invention is prepared according to methods known to the art for the manufacture of solid dispersions, such as fusion/melt technology, hot melt extrusion, solvent evaporation (i.e. freeze drying, spray drying or layering of powders of granules), coprecipitation, supercritical fluid technology and electrostatic spinning method.

The compositions of the invention can also contain other conventional pharmaceutically acceptable compounding ingredients, generally referred to as carriers or diluents, as necessary or desired.

Conventional procedures for preparing such compositions in appropriate dosage forms can be utilized.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan monopalmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnauba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithin, sorbitol monooleate, polyoxyethylene sorbitol monooleate, and polyoxyethylene stearate).

It is believed that one skilled in the art, utilizing the preceding information, can utilize the present invention to its fullest extent.

What is claimed is:

1. A method of treating a hyper-proliferative disorder in a human subject in need thereof comprising orally administering an effective amount of a pharmaceutical combination comprising regorafenib and acetylsalicylic acid, or a hydrate, solvate, or pharmaceutically acceptable salt thereof, or a polymorph thereof, wherein the hyper-proliferative disorder is colorectal cancer, wherein the regorafenib is administered in a dose in an amount of 10 to 100 mg and the acetylsalicylic acid is administered in a dose in an amount of 50 to 100 mg.

2. The method of claim 1, wherein regorafenib and acetylsalicylic acid are administered daily for three weeks and in a fourth week only regorafenib is administered daily.

3. The method of claim 1, wherein the regorafenib and acetylsalicylic acid, or a hydrate, solvate, or pharmaceutically acceptable salt thereof, or a polymorph thereof are administered in separate dosage forms simultaneously or sequentially.

4. The method of claim 1, wherein the total daily dose of regorafenib administered is from 80 to 320 mg/day and the total daily dose of acetylsalicylic acid administered is from 70 to 350 mg/day.

* * * * *